(12) United States Patent
Handique

(10) Patent No.: US 8,110,158 B2
(45) Date of Patent: *Feb. 7, 2012

(54) HEAT-REDUCTION METHODS AND SYSTEMS RELATED TO MICROFLUIDIC DEVICES

(75) Inventor: Kalyan Handique, Ypsilanti, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/904,432

(22) Filed: Oct. 14, 2010

(65) Prior Publication Data

US 2011/0038768 A1 Feb. 17, 2011

Related U.S. Application Data

(63) Continuation of application No. 12/750,471, filed on Mar. 30, 2010, now abandoned, which is a continuation of application No. 12/032,631, filed on Feb. 15, 2008, now abandoned, which is a continuation of application No. 10/778,598, filed on Feb. 17, 2004, now Pat. No. 7,332,130, which is a continuation of application No. 09/783,225, filed on Feb. 14, 2001, now Pat. No. 6,692,700.

(51) Int. Cl.
*B01L 3/00* (2006.01)

(52) U.S. Cl. ........ 422/504; 422/502; 422/503; 422/547; 422/551; 204/193; 204/400; 204/600

(58) Field of Classification Search .................. 422/68.1, 422/82.01, 99, 100, 101, 102, 502, 503, 504, 422/547, 551, 552; 436/147, 174, 180; 204/400, 204/424, 425, 426, 451

See application file for complete search history.

(56) References Cited

U.S. PATENT DOCUMENTS 1,434,314 A 10/1922 Raich
(Continued)

FOREIGN PATENT DOCUMENTS

CA 2294819 1/1999
(Continued)

OTHER PUBLICATIONS

Bollet, C. et al., "A simple method for the isolation of chromosomal DNA from Gram positive or acid-fast bacteria", Nucleic Acids Research, vol. 19, No. 8 (1991), p. 1955.

(Continued)

*Primary Examiner* — Jill Warden
*Assistant Examiner* — Dwayne K Handy
(74) *Attorney, Agent, or Firm* — Knobbe Martens Olson & Bear LLP

(57) ABSTRACT

A system and method for preventing or reducing unwanted heat in a microfluidic of the device while generating heat in selected regions of the device. In one example, current is supplied to a heating element through electric leads, wherein the leads are designed so that the current density in the leads is substantially lower than the current density in the heating element. This maybe accomplished using conductive leads which have a cross-sectional area which is substantially greater than the cross-sectional area of the heating element. In another example, unwanted heat in the microfluidic complex is reduced by thermally isolating the electric leads from the microfluidic complex. This maybe accomplished by running each lead directly away from the microfluidic complex, through a thermally isolating substrate. After the leads pass through the thermally isolating substrate, they are then routed to the current source. Thus, the thermally isolating substrate substantially blocks the transfer of heat from the leads to the microfluidic complex. In another example, unwanted heat is removed from selected regions of the microfluidic complex using one or more cooling devices. One or more Peltier cooling devices may be attached to a substrate to remove heat generated by heating elements and/or other electronic circuitry.

12 Claims, 8 Drawing Sheets

U.S. PATENT DOCUMENTS

| | | | |
|---|---|---|---|
| 1,616,419 A | 2/1927 | Wilson | |
| 1,733,401 A | 8/1930 | Lovekin | |
| 3,528,449 A | 9/1970 | Witte et al. | |
| 3,985,649 A | 10/1976 | Eddelman | |
| 4,018,089 A | 4/1977 | Dzula et al. | |
| 4,018,652 A | 4/1977 | Lanham et al. | |
| 4,038,192 A | 7/1977 | Serur | |
| 4,055,395 A | 10/1977 | Honkawa et al. | |
| D249,706 S | 9/1978 | Adamski | |
| 4,139,005 A | 2/1979 | Dickey | |
| D252,157 S | 6/1979 | Kronish et al. | |
| D252,341 S | 7/1979 | Thomas | |
| D254,687 S | 4/1980 | Fadler et al. | |
| 4,212,744 A | 7/1980 | Oota | |
| D261,033 S | 9/1981 | Armbruster | |
| D261,173 S | 10/1981 | Armbruster | |
| 4,301,412 A | 11/1981 | Hill et al. | |
| 4,439,526 A | 3/1984 | Columbus | |
| 4,457,329 A | 7/1984 | Werley et al. | |
| 4,466,740 A | 8/1984 | Kano et al. | |
| 4,504,582 A | 3/1985 | Swann | |
| 4,522,786 A | 6/1985 | Ebersole | |
| D279,817 S | 7/1985 | Chen et al. | |
| 4,599,315 A | 7/1986 | Terasaki et al. | |
| 4,612,873 A | 9/1986 | Eberle | |
| 4,612,959 A | 9/1986 | Costello | |
| D288,478 S | 2/1987 | Carlson et al. | |
| 4,654,127 A | 3/1987 | Baker et al. | |
| 4,673,657 A | 6/1987 | Christian | |
| 4,683,195 A | 7/1987 | Mullis et al. | |
| 4,683,202 A | 7/1987 | Mullis | |
| D292,735 S | 11/1987 | Lovborg | |
| 4,720,374 A | 1/1988 | Ramachandran | |
| 4,798,693 A | 1/1989 | Mase et al. | |
| 4,800,022 A | 1/1989 | Leonard | |
| D302,294 S | 7/1989 | Hillman | |
| 4,895,650 A | 1/1990 | Wang | |
| 4,919,829 A | 4/1990 | Gates et al. | |
| 4,921,809 A | 5/1990 | Shiff et al. | |
| 4,946,562 A | 8/1990 | Guruswamy | |
| 4,949,742 A | 8/1990 | Rando et al. | |
| D310,413 S | 9/1990 | Bigler et al. | |
| 4,963,498 A | 10/1990 | Hillman | |
| 4,967,950 A | 11/1990 | Legg et al. | |
| 4,978,502 A | 12/1990 | Dole et al. | |
| 4,978,622 A | 12/1990 | Mishell et al. | |
| 4,989,626 A | 2/1991 | Takagi et al. | |
| 5,001,417 A | 3/1991 | Pumphrey et al. | |
| 5,004,583 A | 4/1991 | Guruswamy et al. | |
| 5,048,554 A | 9/1991 | Kremer | |
| 5,053,199 A | 10/1991 | Keiser et al. | |
| 5,060,823 A | 10/1991 | Perlman | |
| 5,061,336 A | 10/1991 | Soane | |
| 5,064,618 A | 11/1991 | Baker et al. | |
| 5,071,531 A | 12/1991 | Soane | |
| 5,091,328 A | 2/1992 | Miller | |
| D324,426 S | 3/1992 | Fan et al. | |
| 5,096,669 A | 3/1992 | Lauks et al. | |
| 5,126,002 A | 6/1992 | Iwata et al. | |
| 5,126,022 A | 6/1992 | Soane et al. | |
| D328,135 S | 7/1992 | Fan et al. | |
| D328,794 S | 8/1992 | Frenkel et al. | |
| 5,135,627 A | 8/1992 | Soane | |
| 5,135,872 A | 8/1992 | Pouletty et al. | |
| 5,147,606 A | 9/1992 | Charlton et al. | |
| 5,169,512 A | 12/1992 | Wiedenmann et al. | |
| D333,522 S | 2/1993 | Gianino | |
| 5,186,339 A | 2/1993 | Heissler | |
| 5,192,507 A | 3/1993 | Taylor et al. | |
| 5,208,163 A | 5/1993 | Charlton et al. | |
| 5,223,226 A | 6/1993 | Wittmer et al. | |
| D338,275 S | 8/1993 | Fischer et al. | |
| 5,250,263 A | 10/1993 | Manz | |
| 5,252,743 A | 10/1993 | Barrett et al. | |
| 5,256,376 A | 10/1993 | Callan et al. | |
| 5,275,787 A | 1/1994 | Yuguchi et al. | |
| 5,282,950 A | 2/1994 | Dietze et al. | |
| 5,296,375 A | 3/1994 | Kricka et al. | |
| 5,304,477 A | 4/1994 | Nagoh et al. | |
| 5,304,487 A | 4/1994 | Wilding et al. | |
| D347,478 S | 5/1994 | Pinkney | |
| 5,311,896 A | 5/1994 | Kaartinen et al. | |
| 5,311,996 A | 5/1994 | Duffy et al. | |
| 5,316,727 A | 5/1994 | Suzuki et al. | |
| 5,327,038 A | 7/1994 | Culp | |
| 5,339,486 A | 8/1994 | Persic, Jr. | |
| D351,913 S | 10/1994 | Hieb et al. | |
| 5,364,591 A | 11/1994 | Green et al. | |
| 5,372,946 A | 12/1994 | Cusak et al. | |
| 5,374,395 A | 12/1994 | Robinson | |
| 5,389,339 A | 2/1995 | Petschek et al. | |
| 5,401,465 A | 3/1995 | Smethers et al. | |
| 5,411,708 A | 5/1995 | Moscetta et al. | |
| 5,416,000 A | 5/1995 | Allen et al. | |
| 5,422,271 A | 6/1995 | Chen et al. | |
| 5,422,284 A | 6/1995 | Lau | |
| 5,427,946 A | 6/1995 | Kricka et al. | |
| 5,474,796 A | 12/1995 | Brennan | |
| D366,116 S | 1/1996 | Biskupski | |
| 5,486,335 A | 1/1996 | Wilding et al. | |
| 5,494,639 A | 2/1996 | Grzegorzewski | |
| 5,498,392 A | 3/1996 | Wilding et al. | |
| 5,503,803 A | 4/1996 | Brown | |
| 5,516,410 A | 5/1996 | Schneider et al. | |
| 5,519,635 A | 5/1996 | Miyake et al. | |
| 5,529,677 A | 6/1996 | Schneider et al. | |
| 5,559,432 A | 9/1996 | Logue | |
| 5,565,171 A | 10/1996 | Dovichi et al. | |
| 5,569,364 A | 10/1996 | Hooper et al. | |
| 5,578,818 A | 11/1996 | Kain et al. | |
| 5,580,523 A | 12/1996 | Bard | |
| 5,582,884 A | 12/1996 | Ball et al. | |
| 5,585,069 A | 12/1996 | Zanucchi et al. | |
| 5,585,089 A | 12/1996 | Queen et al. | |
| 5,585,242 A | 12/1996 | Bouma et al. | |
| 5,587,128 A | 12/1996 | Wilding et al. | |
| 5,589,136 A | 12/1996 | Northrup et al. | |
| 5,593,838 A | 1/1997 | Zanzucchi et al. | |
| 5,595,708 A | 1/1997 | Berndt | |
| 5,599,432 A | 2/1997 | Manz et al. | |
| 5,599,503 A | 2/1997 | Manz et al. | |
| 5,599,667 A | 2/1997 | Arnold, Jr. et al. | |
| 5,601,727 A | 2/1997 | Bormann et al. | |
| 5,603,351 A | 2/1997 | Cherukuri et al. | |
| 5,605,662 A | 2/1997 | Heller et al. | |
| D378,782 S | 4/1997 | LaBarbera et al. | |
| 5,628,890 A | 5/1997 | Carter et al. | |
| 5,630,920 A | 5/1997 | Friese et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,639,423 A | 6/1997 | Northrup et al. | |
| 5,643,738 A | 7/1997 | Zanzucchi et al. | |
| 5,646,039 A | 7/1997 | Northrup et al. | |
| 5,647,994 A | 7/1997 | Tuunanen et al. | |
| 5,651,839 A | 7/1997 | Rauf | |
| 5,652,149 A | 7/1997 | Mileaf et al. | |
| D382,346 S | 8/1997 | Buhler et al. | |
| D382,647 S | 8/1997 | Staples et al. | |
| 5,667,976 A | 9/1997 | Van Ness et al. | |
| 5,671,303 A | 9/1997 | Shieh et al. | |
| 5,674,394 A | 10/1997 | Whitmore | |
| 5,674,742 A | 10/1997 | Northrup et al. | |
| 5,681,484 A | 10/1997 | Zanzucchi et al. | |
| 5,681,529 A | 10/1997 | Taguchi et al. | |
| 5,683,657 A | 11/1997 | Mian | |
| 5,699,157 A | 12/1997 | Parce | |
| 5,700,637 A | 12/1997 | Southern | |
| 5,705,813 A | 1/1998 | Apffel et al. | |
| 5,726,026 A | 3/1998 | Wilding et al. | |
| 5,726,404 A | 3/1998 | Brody | |
| 5,726,944 A | 3/1998 | Taft et al. | |
| 5,731,212 A | 3/1998 | Gavin et al. | |
| 5,744,366 A | 4/1998 | Kricka et al. | |
| 5,747,666 A | 5/1998 | Willis | |

| Patent | Kind | Date | Inventors |
|---|---|---|---|
| 5,750,015 | A | 5/1998 | Soane et al. |
| 5,755,942 | A | 5/1998 | Zanzucchi et al. |
| 5,763,262 | A | 6/1998 | Wong et al. |
| 5,770,029 | A | 6/1998 | Nelson et al. |
| 5,770,388 | A | 6/1998 | Vorpahl |
| 5,772,966 | A | 6/1998 | Maracas et al. |
| 5,779,868 | A | 7/1998 | Parce et al. |
| 5,787,032 | A | 7/1998 | Heller et al. |
| 5,788,814 | A | 8/1998 | Sun et al. |
| 5,800,690 | A | 9/1998 | Chow et al. |
| D399,959 | S | 10/1998 | Prokop et al. |
| 5,827,481 | A | 10/1998 | Bente et al. |
| 5,842,106 | A | 11/1998 | Thaler et al. |
| 5,842,787 | A | 12/1998 | Kopf-Sill et al. |
| 5,846,396 | A | 12/1998 | Zanzucchi et al. |
| 5,849,208 | A | 12/1998 | Hayes et al. |
| 5,849,486 | A | 12/1998 | Heller et al. |
| 5,849,489 | A | 12/1998 | Heller |
| 5,849,598 | A | 12/1998 | Wilson et al. |
| 5,852,495 | A | 12/1998 | Parce |
| 5,856,174 | A | 1/1999 | Lipshutz et al. |
| 5,858,188 | A | 1/1999 | Soane et al. |
| 5,863,502 | A | 1/1999 | Southgate et al. |
| 5,863,708 | A | 1/1999 | Zanzucchi et al. |
| 5,863,801 | A | 1/1999 | Southgate et al. |
| 5,866,345 | A | 2/1999 | Wilding et al. |
| 5,869,004 | A | 2/1999 | Parce et al. |
| 5,872,010 | A | 2/1999 | Karger et al. |
| 5,874,046 | A | 2/1999 | Megerle |
| 5,876,675 | A | 3/1999 | Kennedy |
| 5,880,071 | A | 3/1999 | Parce et al. |
| 5,882,465 | A | 3/1999 | McReynolds |
| 5,883,211 | A | 3/1999 | Sassi et al. |
| 5,885,432 | A | 3/1999 | Hooper et al. |
| 5,885,470 | A | 3/1999 | Parce et al. |
| 5,895,762 | A | 4/1999 | Greenfield et al. |
| 5,900,130 | A | 5/1999 | Benregnu et al. |
| 5,912,124 | A | 6/1999 | Kumar |
| 5,912,134 | A | 6/1999 | Shartle |
| 5,916,522 | A | 6/1999 | Boyd et al. |
| 5,916,776 | A | 6/1999 | Kumar |
| 5,919,711 | A | 7/1999 | Boyd et al. |
| 5,922,591 | A | 7/1999 | Anderson et al. |
| 5,927,547 | A | 7/1999 | Papen et al. |
| 5,928,880 | A | 7/1999 | Wilding et al. |
| 5,929,208 | A | 7/1999 | Heller et al. |
| D413,391 | S | 8/1999 | Lapeus et al. |
| 5,932,799 | A | 8/1999 | Moles |
| 5,935,401 | A | 8/1999 | Amigo |
| 5,939,291 | A | 8/1999 | Loewy et al. |
| 5,942,443 | A | 8/1999 | Parce et al. |
| D413,677 | S | 9/1999 | Dumitrescu et al. |
| 5,948,227 | A | 9/1999 | Dubrow |
| 5,955,028 | A | 9/1999 | Chow |
| 5,955,029 | A | 9/1999 | Wilding et al. |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,221 | A | 9/1999 | Boyd et al. |
| 5,959,291 | A | 9/1999 | Jensen |
| 5,964,995 | A | 10/1999 | Nikiforov et al. |
| 5,964,997 | A | 10/1999 | McBride |
| 5,965,001 | A | 10/1999 | Chow et al. |
| 5,965,410 | A | 10/1999 | Chow et al. |
| 5,965,886 | A | 10/1999 | Sauer et al. |
| 5,972,187 | A | 10/1999 | Parce et al. |
| D417,009 | S | 11/1999 | Boyd |
| 5,976,336 | A | 11/1999 | Dubrow et al. |
| 5,980,704 | A | 11/1999 | Cherukuri et al. |
| 5,980,719 | A | 11/1999 | Cherukuri et al. |
| 5,981,735 | A | 11/1999 | Thatcher et al. |
| 5,989,402 | A | 11/1999 | Chow et al. |
| 5,992,820 | A | 11/1999 | Fare et al. |
| 5,993,611 | A | 11/1999 | Moroney, III et al. |
| 5,993,750 | A | 11/1999 | Ghosh et al. |
| 5,997,708 | A | 12/1999 | Craig |
| 6,001,231 | A | 12/1999 | Kopf-Sill |
| 6,001,307 | A | 12/1999 | Naka et al. |
| 6,004,515 | A | 12/1999 | Parce et al. |
| 6,007,690 | A | 12/1999 | Nelson et al. |
| 6,010,627 | A | 1/2000 | Hood, III |
| 6,012,902 | A | 1/2000 | Parce |
| D420,747 | S | 2/2000 | Dumitrescu et al. |
| D421,130 | S | 2/2000 | Cohen et al. |
| 6,024,920 | A | 2/2000 | Cunanan |
| D421,653 | S | 3/2000 | Purcell |
| 6,033,546 | A | 3/2000 | Ramsey |
| 6,043,080 | A | 3/2000 | Lipshutz et al. |
| 6,046,056 | A | 4/2000 | Parce et al. |
| 6,048,734 | A | 4/2000 | Burns et al. |
| 6,054,034 | A | 4/2000 | Soane et al. |
| 6,054,277 | A | 4/2000 | Furcht et al. |
| 6,056,860 | A | 5/2000 | Amigo et al. |
| 6,057,149 | A | 5/2000 | Burns et al. |
| 6,063,341 | A | 5/2000 | Fassbind et al. |
| 6,063,589 | A | 5/2000 | Kellogg et al. |
| 6,071,478 | A | 6/2000 | Chow |
| D428,497 | S | 7/2000 | Lapeus et al. |
| 6,086,740 | A | 7/2000 | Kennedy |
| 6,102,897 | A | 8/2000 | Lang |
| 6,106,685 | A | 8/2000 | McBride et al. |
| 6,123,205 | A | 9/2000 | Dumitrescu et al. |
| 6,130,098 | A | 10/2000 | Handique et al. |
| 6,132,580 | A | 10/2000 | Mathies et al. |
| 6,132,684 | A | 10/2000 | Marino |
| 6,133,436 | A | 10/2000 | Koster et al. |
| D433,759 | S | 11/2000 | Mathis et al. |
| 6,143,250 | A | 11/2000 | Tajima |
| 6,156,199 | A | 12/2000 | Zuk, Jr. |
| 6,168,948 | B1 | 1/2001 | Anderson et al. |
| 6,171,850 | B1 | 1/2001 | Nagle et al. |
| 6,174,675 | B1 | 1/2001 | Chow et al. |
| D438,311 | S | 2/2001 | Yamanishi et al. |
| D438,632 | S | 3/2001 | Miller |
| D438,633 | S | 3/2001 | Miller |
| 6,197,595 | B1 | 3/2001 | Anderson et al. |
| 6,211,989 | B1 | 4/2001 | Wulf et al. |
| 6,221,600 | B1 | 4/2001 | MacLeod et al. |
| 6,235,175 | B1 | 5/2001 | Dubrow et al. |
| 6,235,313 | B1 | 5/2001 | Mathiowitz et al. |
| 6,236,581 | B1 | 5/2001 | Lines et al. |
| 6,251,343 | B1 | 6/2001 | Dubrow et al. |
| 6,254,826 | B1 | 7/2001 | Acosta et al. |
| 6,259,635 | B1 | 7/2001 | Torelli et al. |
| 6,261,431 | B1 | 7/2001 | Mathies et al. |
| D446,306 | S | 8/2001 | Ochi et al. |
| 6,271,021 | B1 | 8/2001 | Burns et al. |
| 6,274,089 | B1 | 8/2001 | Chow et al. |
| 6,281,008 | B1 | 8/2001 | Komai et al. |
| 6,287,254 | B1 | 9/2001 | Dodds |
| 6,291,248 | B1 | 9/2001 | Haj-Ahmad |
| 6,294,063 | B1 | 9/2001 | Becker et al. |
| 6,302,134 | B1 | 10/2001 | Kellogg et al. |
| 6,302,304 | B1 | 10/2001 | Spencer |
| 6,306,273 | B1 | 10/2001 | Wainright et al. |
| 6,319,469 | B1 | 11/2001 | Mian et al. |
| 6,326,211 | B1 | 12/2001 | Anderson et al. |
| 6,337,435 | B1 | 1/2002 | Chu et al. |
| 6,368,871 | B1 | 4/2002 | Christel et al. |
| 6,370,206 | B1 | 4/2002 | Schenk |
| 6,375,901 | B1 | 4/2002 | Robotti et al. |
| 6,379,929 | B1 | 4/2002 | Burns et al. |
| 6,379,974 | B1 | 4/2002 | Parce et al. |
| 6,391,541 | B1 | 5/2002 | Petersen et al. |
| 6,391,623 | B1 | 5/2002 | Besemer et al. |
| 6,395,161 | B1 | 5/2002 | Schneider et al. |
| 6,398,956 | B1 | 6/2002 | Coville et al. |
| 6,399,025 | B1 | 6/2002 | Chow |
| 6,399,389 | B1 | 6/2002 | Parce et al. |
| 6,403,338 | B1 | 6/2002 | Knapp et al. |
| 6,408,878 | B2 | 6/2002 | Unger et al. |
| D461,906 | S | 8/2002 | Pham |
| 6,428,987 | B2 | 8/2002 | Franzen |
| 6,432,366 | B2 | 8/2002 | Ruediger et al. |
| 6,440,725 | B1 | 8/2002 | Pourahmadi et al. |
| 6,444,461 | B1 | 9/2002 | Knapp et al. |
| 6,448,064 | B1 | 9/2002 | Vo-Dinh et al. |
| 6,453,928 | B1 | 9/2002 | Kaplan et al. |

| | | |
|---|---|---|
| 6,498,497 B1 | 12/2002 | Chow et al. |
| 6,500,390 B1 | 12/2002 | Boulton et al. |
| D468,437 S | 1/2003 | McMenamy et al. |
| 6,509,193 B1 | 1/2003 | Tajima |
| 6,521,188 B1 | 2/2003 | Webster |
| 6,544,734 B1 | 4/2003 | Briscoe et al. |
| 6,572,830 B1 | 6/2003 | Burdon et al. |
| 6,579,453 B1 | 6/2003 | Bächler et al. |
| 6,597,450 B1 | 7/2003 | Andrews et al. |
| 6,602,474 B1 | 8/2003 | Tajima |
| 6,692,700 B2 * | 2/2004 | Handique ............ 422/100 |
| 6,706,519 B1 * | 3/2004 | Kellogg et al. ............ 435/287.2 |
| 6,734,401 B2 * | 5/2004 | Bedingham et al. ............ 219/388 |
| 6,783,962 B1 | 8/2004 | Olander et al. |
| 6,878,540 B2 | 4/2005 | Pourahmadi et al. |
| 6,911,183 B1 | 6/2005 | Handique et al. |
| 6,914,137 B2 | 7/2005 | Baker |
| 6,942,771 B1 | 9/2005 | Kayyem |
| 7,235,406 B1 | 6/2007 | Woudenberg et al. |
| 7,332,130 B2 * | 2/2008 | Handique ............ 422/102 |
| 2001/0023848 A1 | 9/2001 | Gjerde et al. |
| 2001/0038450 A1 | 11/2001 | McCaffrey et al. |
| 2001/0046702 A1 | 11/2001 | Schmebri |
| 2001/0055765 A1 | 12/2001 | O'Keefe et al. |
| 2002/0001848 A1 | 1/2002 | Bedingham et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0060156 A1 | 5/2002 | Mathies et al. |
| 2002/0068357 A1 | 6/2002 | Mathies et al. |

FOREIGN PATENT DOCUMENTS

| | | |
|---|---|---|
| DE | 19929734 | 12/1999 |
| EP | 0766256 | 4/1997 |
| FR | 2672301 | 8/1992 |
| FR | 2795426 | 12/2000 |
| JP | 58212921 A | 12/1983 |
| WO | WO 88/06633 | 9/1988 |
| WO | WO 92/05443 | 4/1992 |
| WO | WO 98/00231 | 1/1998 |
| WO | WO 98/22625 | 5/1998 |
| WO | WO 98/53311 | 11/1998 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/078845 | 10/2002 |
| WO | WO 03/012325 | 2/2003 |
| WO | WO 03/012406 | 2/2003 |
| WO | WO 03/055605 | 7/2003 |
| WO | WO 2004/007081 | 1/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2008/060604 | 5/2008 |
| WO | WO 2009/012185 | 1/2009 |

OTHER PUBLICATIONS

Brahmassandra, et al., On-Chip DNA Detection in Microfabricated Separation Systems, Part of the SPIE Conference on Microfludic Devices and Systems, 1998, Santa Clara, California, vol. 3515, pp. 242-251.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Broyles, et al., "Sample Filtration, Concentration, and Separation Integrated on Microfluidic Devices" Analytical Chemistry (American Chemical Society), vol. 75 No. 11: pp. 2761-2767, 2003.

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

* cited by examiner

*Fig. 5*
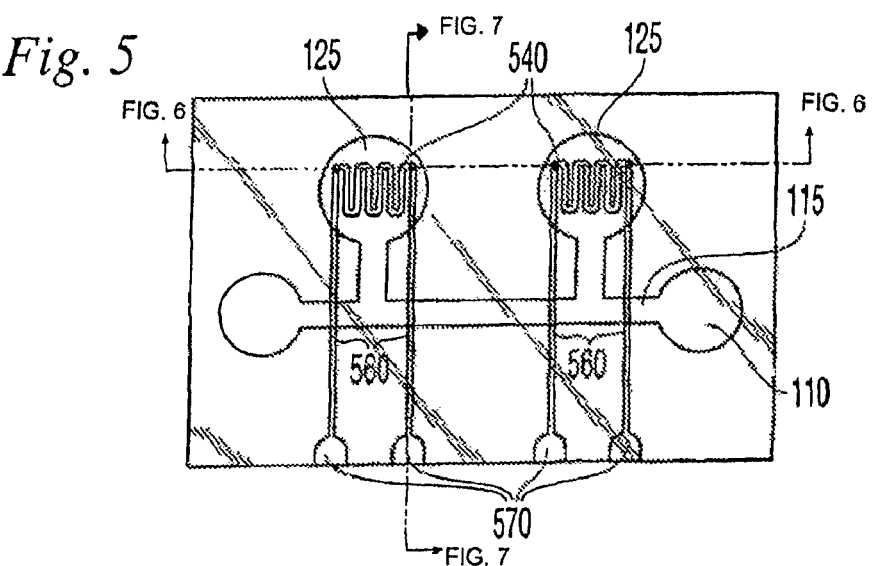
*Fig. 6*
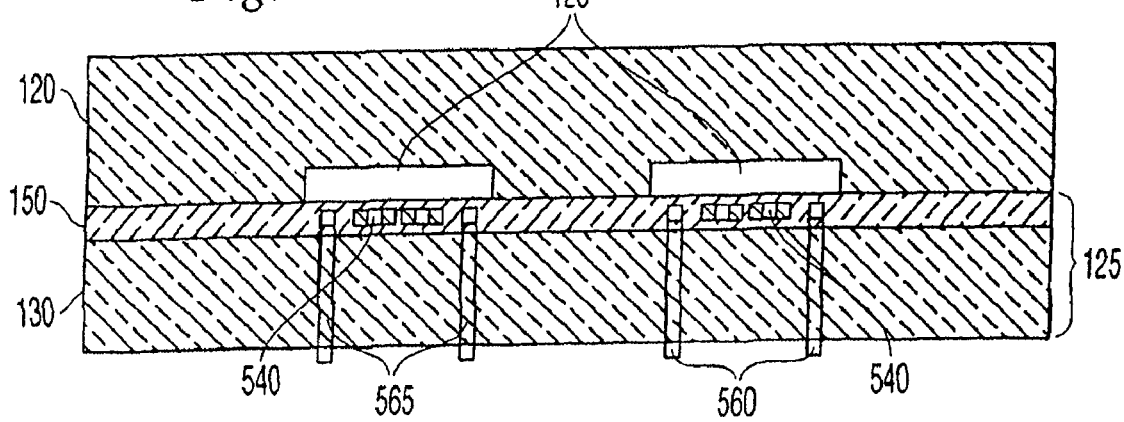
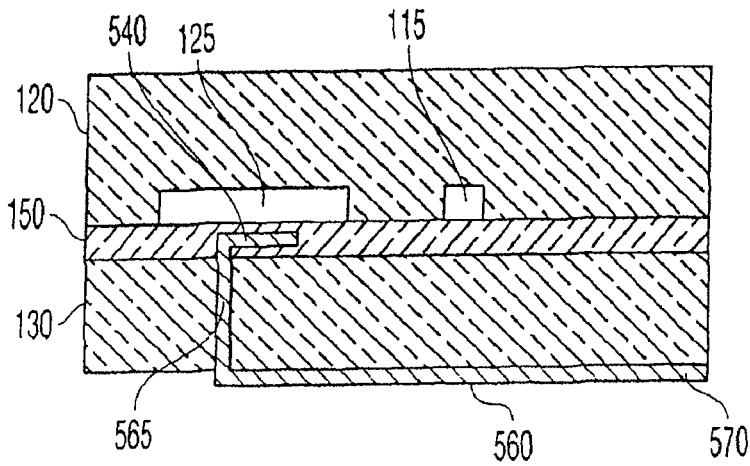
*Fig. 7*

*Fig. 13*
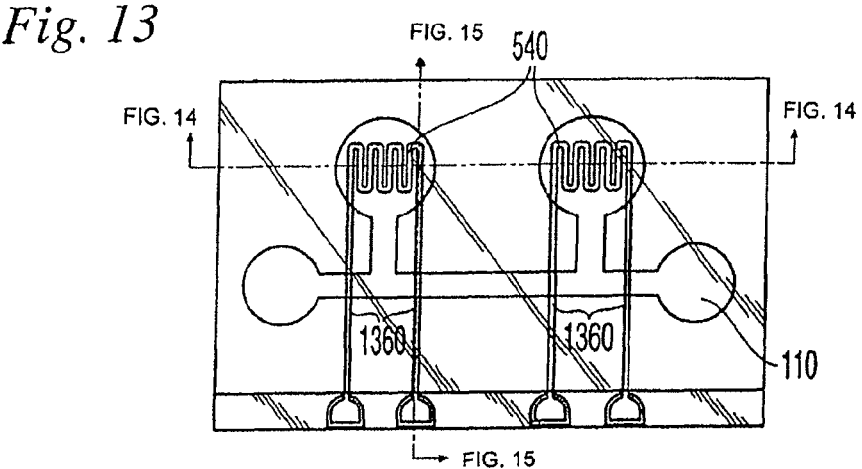
*Fig. 14*
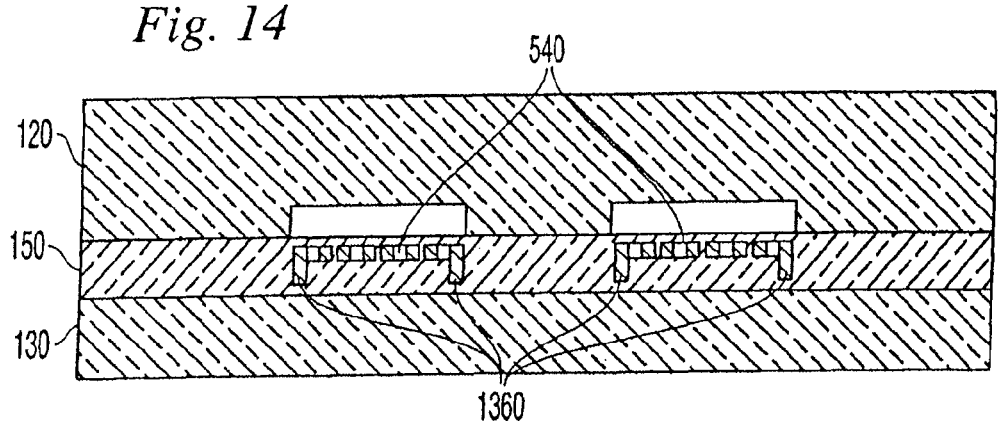
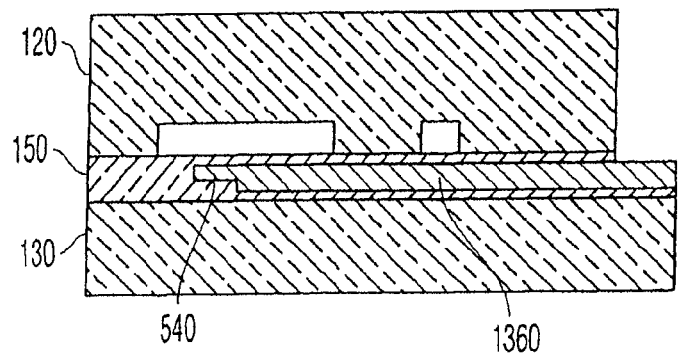
*Fig. 15*

HEAT-REDUCTION METHODS AND SYSTEMS RELATED TO MICROFLUIDIC DEVICES

CROSS-REFERENCE TO RELATED APPLICATIONS

This application is a continuation of and claims the benefit of priority of U.S. application Ser. No. 12/750,471, filed Mar. 30, 2010, which is a continuation of U.S. application Ser. No. 12/032,631, filed Feb. 15, 2008, which is a continuation of U.S. application Ser. No. 10/778,598, filed Feb. 17, 2004, now U.S. Pat. No. 7,332,130, which is a continuation of U.S. application Ser. No. 09/783,225, filed Feb. 14, 2001, now U.S. Pat. No. 6,692,700, the entire contents of which are hereby incorporated by reference.

BACKGROUND OF THE INVENTION

1. Field of the Invention

The present invention relates to microfluidic devices, and more particularly to heat management in such devices.

2. Description of the Related Art

Microfluidic devices are known. For example, U.S. Pat. No. 6,130,098 ("the '098 patent") (the contents of which are incorporated herein in their entirety by reference) discloses microfluidic devices that include microdroplet channels for transporting fluid droplets through a fluid processing system. The system includes a variety of microscale components for processing the fluid droplets, including micro-reaction chambers, electrophoresis modules, and detectors (such as radiation detectors). In some embodiments, the devices also include air chambers to internally generate air pressure to automatically withdraw a measured volume of fluid from an input port.

Typically, these elements are microfabricated from silicon, glass, ceramic, plastic, and/or quartz substrates. The various fluid-processing components are linked by microchannels, through which the fluid droplets flow under the control of a fluid propulsion mechanism. If the substrate is formed from silicon, electronic components may be fabricated on the same substrate, allowing sensors and controlling circuitry to be incorporated in the same device. Since all of the components are made using conventional photolithographic techniques, multi-component devices can be readily assembled into complex, integrated systems.

Microfluidic devices use heating elements to accomplish a variety of tasks. For example, U.S. Pat. No. 6,130,098 discloses devices that use heating elements to automatically withdraw a measured volume of fluid from a fluid input port. Liquid placed into a fluid port flows into a channel, past a chamber connected to the side of the channel, and stops at a hydrophobic patch on the wall of the channel. The chamber is then heated, causing pressure to build up. Once the pressure reaches a particular threshold, a microdroplet splits from the rest of the liquid, and is pushed over the hydrophobic patch and down the channel for further processing.

Heating elements can also be used to move such a measured microfluidic droplet through an etched channel. This can be accomplished using a heat-controlled pressure chamber as described in the '098 patent. Fluid movement can also be performed using a series of heaters to generate thermal gradients to change the interfacial tension at the front or back of the droplets, thereby generating a pressure difference across the droplet. For example, a droplet can be propelled forward by heating the back interface. The local increase in temperature reduces the surface tension on the back surface of the droplet and decreases the interfacial pressure difference. The decreased pressure difference corresponds to an increase in the local internal pressure on that end of the droplet. The two droplet interfaces (front and back) are no longer in equilibrium, and the pressure difference propels the droplet forward. Forward motion can be maintained by continuing to heat the droplet at the rear surface with successive heaters along the channel (see FIG. 5 of U.S. Pat. No. 6,130,098), while heating the opposite surface can be used to reverse the motion of the droplet.

Other heater elements may be used to control the temperature in reaction chambers, for example, to perform PCR. Others may be used to manipulate valves made of meltable material (such as wax or solder) as described in U.S. Pat. No. 6,048,734.

All such heater elements, when heating a particular region of a microfluidic device, tend to generate unwanted heat in other regions of the device. Such unwanted heat may adversely affect operation of the microfluidic devices. For example, too much heat can adversely affect the properties of a liquid or gas being processed.

SUMMARY OF THE INVENTION

The invention relates to a system and method for preventing or reducing unwanted heat in a microfluidic device while generating heat in selected regions of the device.

In one aspect, the invention involves supplying current to a heating element through electric leads, wherein the leads are designed so that the current density in the leads is substantially lower than the current density in the heating element. In a preferred embodiment, this is accomplished using conductive leads which have a cross-sectional area which is substantially greater than the cross-sectional area of the heating element.

In another aspect, the invention involves reducing the amount of unwanted heat in the microfluidic complex by thermally isolating the electric leads from the microfluidic complex. In a preferred embodiment, this is accomplished by running each lead directly away from the microfluidic complex, through a thermally isolating substrate. After passing through the thermally isolating substrate, the leads are then routed to the current source. Thus, the thermally isolating substrate substantially blocks the transfer of heat from the leads to the microfluidic complex.

In another aspect, the invention involves removing unwanted heat from selected regions of the microfluidic complex using one or more cooling devices. In a preferred embodiment, one or more Peltier cooling devices are attached to a substrate to remove heat generated by heating elements and/or other electronic circuitry.

BRIEF DESCRIPTION OF THE DRAWINGS

FIG. 5 shows a top-down view of a device comprising a preferred embodiment of the present invention.

FIG. 6 shows a cross-sectional end view of the device in FIG. 5.

FIG. 7 shows a cross-sectional side view of the device in FIG. 5.

FIG. 13 depicts a top-down view of a device comprising a further preferred embodiment of the present invention.

FIG. 14 depicts a cross-sectional end view of the device in FIG. 13.

FIG. 15 depicts a cross-sectional side view of the device in FIG. 13.

DETAILED DESCRIPTION OF PREFERRED EMBODIMENTS

The present invention relates to microfluidic devices, and in particular, heat management in such devices.

Microfluidic devices typically include micromachined fluid networks in an integrated analysis system. Fluid samples and reagents are brought into the device through entry ports and transported through channels to a reaction chamber, such as a thermally controlled reactor where mixing and reactions (e.g., restriction enzyme digestion or nucleic acid amplification) occur. The biochemical products may then be moved, for example, to an electrophoresis module, where migration data is collected by a detector and transmitted to a recording instrument. The fluidic and electronic components are preferably designed to be fully compatible in function and construction with the biological reactions and reagents.

Figure 1:
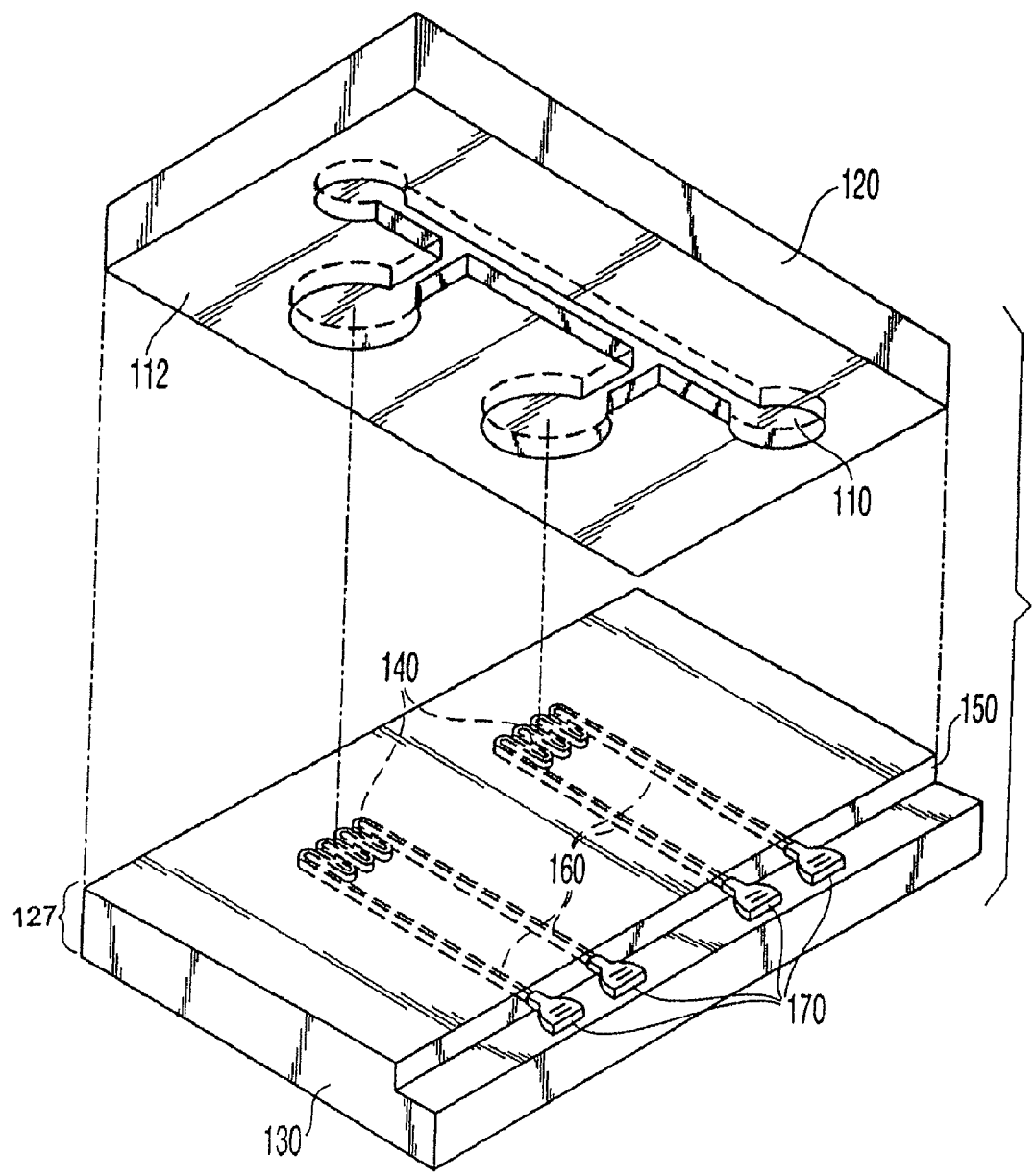
FIG. 1 is an expanded view of a microfluidic device as is known in the art.

There are many formats, materials, and size scales for constructing such integrated micro-fluidic systems. FIG. 1 shows an expanded view of a simple microfluidic device, which will be used to illustrate some of the heat management techniques of the present invention. The device includes an upper substrate 120, which is bonded to a lower substrate 127 to form a fluid network (see FIGS. 2-4).

The upper substrate 120 depicted in FIG. 1 is preferably formed of glass and has a microfluidic complex 110 in its bottom surface 112. Those skilled in the art will recognize that substrates composed of silicon, glass, ceramics, plastic, and/or quartz are all acceptable in the context of the present invention.

Microfluidic complex 110 includes a plurality of chambers connected by a network of microchannels. The number of chambers and channels, as well as the overall topology of the microfluidic complex, will depend upon the particular application which the microfluidic device is designed to perform. However, FIG. 1 depicts a simple microfluidic complex for purposes of illustrating the heat management techniques of the present invention, and is not intended to depict a microfluidic complex for any particular application.

The channels and chambers of the microfluidic complex are etched in the bottom surface 112 of the glass substrate 120 using known photolithographic techniques. More specifically, transparent templates or masks containing opaque designs are used to photo-define objects on the surface of the substrate. The patterns on the templates are generated with computer-aided-design programs and can delineate structures with line-widths of less than one micron. Once a template is generated, it can be used almost indefinitely to produce identical replicate structures. Consequently, even extremely complex microfluidic complexes can be reproduced in mass quantities and at low incremental unit cost.

The lower substrate 127 includes a glass base 130 and an oxide layer 150. Within oxide layer 150, resistive heaters 140 and electric leads 160 are formed. The leads 160 connect to terminals 170 which are exposed at the edge of the substrate to permit electrical connection to an external voltage source (not shown) that controls the heaters. More specifically, to activate a heater 140, a voltage is applied across a pair of terminals 170 to supply current through leads 160 and heater 140, thereby heating the resistive heater element 140. However, since the same current passes through leads 160, these leads are also heated.

Metal heater elements 140 are positioned so that, when the upper and lower substrates are bonded together, the heaters reside directly beneath the fluid chambers of the upper substrate so as to be able to heat the contents of the microchambers. The silicon oxide layer 150 prevents the heating elements 140 from directly contacting with fluid in the microfluidic complex 110.

The oxide layer 150, heating elements 140, and resistive leads 160 are fabricated using well-known photolithographic techniques, such as those used to etch microfluidic complex 110.

Figure 2:
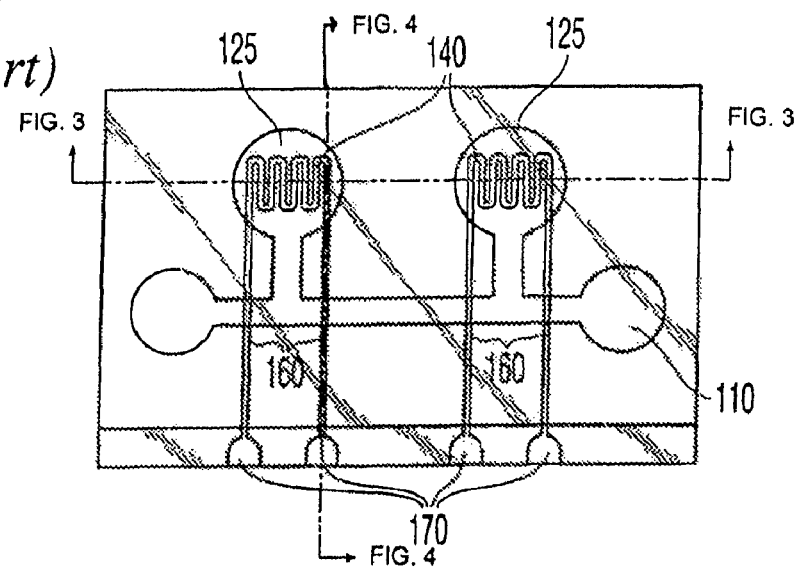
FIG. 2 shows a top-down view of the device in FIG. 1, assembled.
Figure 3:
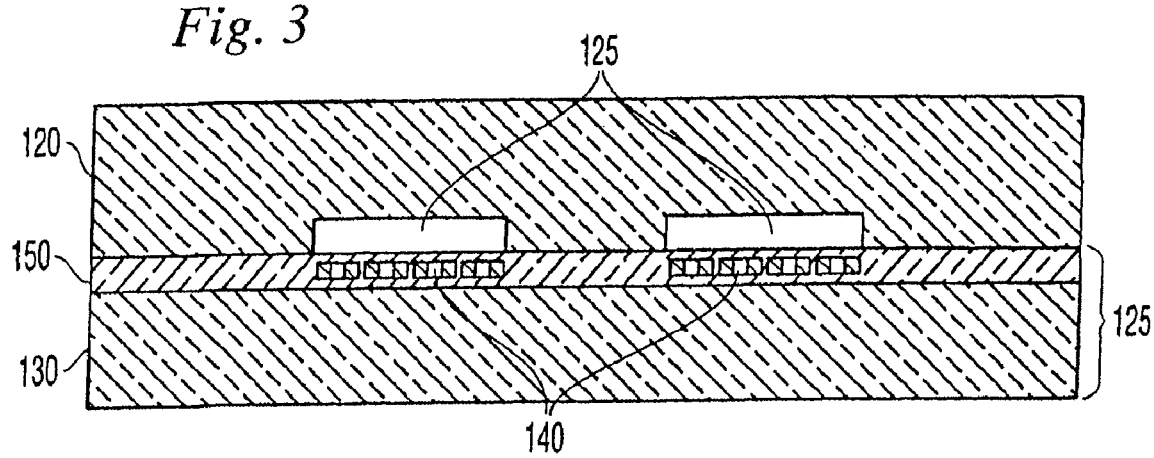
FIG. 3 shows a cross-sectional end view of the device in FIG. 2.

FIG. 2 is a top-down view of the device in FIG. 1. In this figure, upper substrate 120 is shown atop substrate 127 and silicon oxide layer 150. Each microchamber 125 of the microfluidic complex is directly above a corresponding heater element 140 to allow the heater to raise the temperature of the contents of the chamber. (This relationship is shown more clearly in the cross-sectional end view of the device depicted in FIG. 3).

However, as shown in FIG. 2, the leads 160 (which supply current to the heaters) pass directly beneath microchannel 115. This relationship is more clearly shown in cross-sectional side view of the device depicted in FIG. 4.

Figure 4:
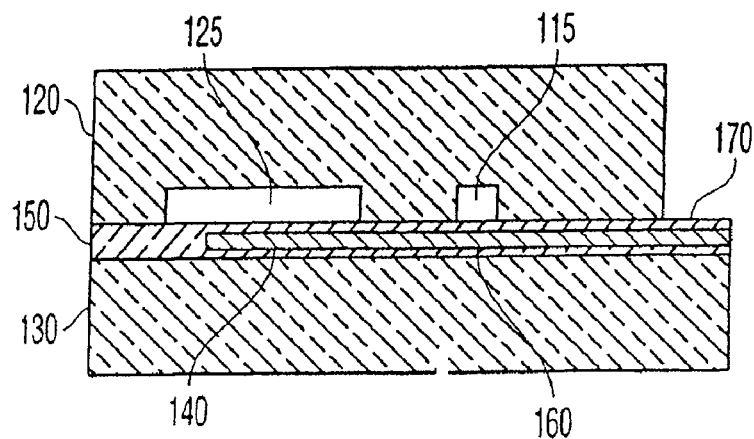
FIG. 4 shows a cross-sectional side view of the device in FIG. 2.
Figure 8:
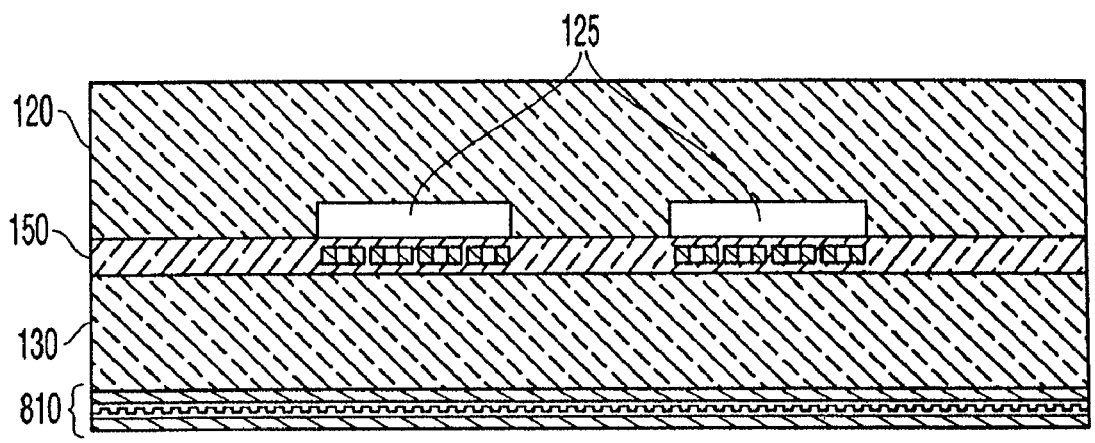
FIG. 8 depicts the device in FIG. 3, with a Peltier device attached to the lower substrate.
Figure 9:
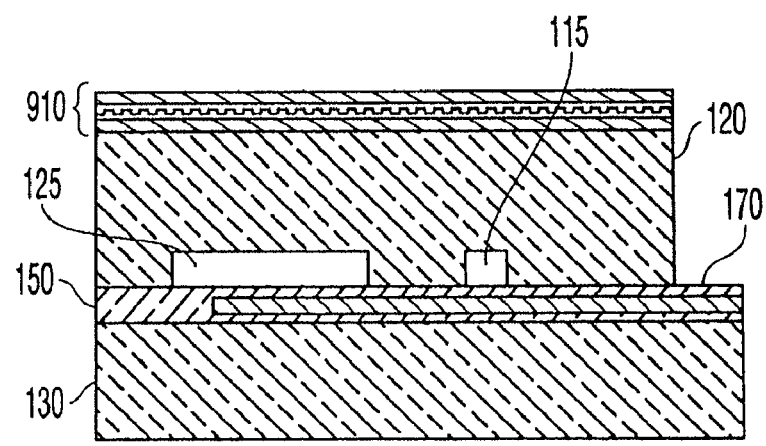
FIG. 9 depicts the device in FIG. 4, with a Peltier device attached to the upper substrate.

FIG. 4 clearly shows the leads 160 positioned beneath microchannel 115 and separated from the channel 115 by only a thin layer of oxide. Thus, the leads 160, when carrying current to heater 140, may warm any fluid (or gas or meltable material) in the microchannel 115, thereby possibly adversely affecting the operation of the microfluidic device.

Referring again to FIG. 2, the heater leads 160 also run close to the channels connecting chambers 125 to channel 115. Accordingly, when the leads are supplying electric current to heater 140, they may also unintentionally warm the contents of any fluid or wax in the side channels.

FIGS. 5-7 depict the structure of a first preferred embodiment of the invention which eliminates, or at least substantially reduces, such unwanted heat from the leads. In this structure, the resistive heating elements 540 reside in the oxide layer directly beneath chamber 125, just as they do in the structure shown in FIG. 2. However, unlike the structure of FIG. 2, the electrical leads do NOT reside in the oxide layer 150. Rather, as shown in FIG. 6, the leads 565 first pass directly through the oxide layer 150 and glass base 130 to the opposite side of the substrate 130 (herein "vertical leads").

Preferably the vertical leads 565 are orthogonal to the plane in which heater elements 540 reside.

The vertical leads 565 are then connected to horizontal leads 560, which run along the opposite side of substrate 130 and connect to terminals 570 as shown in FIG. 7. Also as shown in FIG. 7, horizontal leads 560 run under channel 115. However, they are now separated from the channel by the full oxide layer 150 and base 130 which act as a thermal isolating layer. Base 130 and oxide 150 should collectively have a sufficiently low thermal conductivity to substantially prevent heat emitted by the leads on the bottom of substrate 130 from adversely affecting the operation of the microfluidic complex 110. Thus, this configuration substantially reduces the amount of heat transmitted from the leads 560 to the microfluidic complex 110.

Those skilled in the art will recognize that the above described technique is not limited to microfluidic devices formed from a pair of substrates, such as shown in FIG. Rather, the technique is generally useful in microfluidic devices for reducing unwanted transfer of heat generated by the electric leads. Regardless of how the microfluidic complex is formed, unwanted heat transfer is reduced if the electric leads are routed from the terminals of the heating element through a thermally resistive material, such that the leads are substantially isolated from the microfluidic complex.

The vertical leads shown in FIGS. 5 and 6 may be formed by drilling holes through substrate 130 before oxide layer 150 and heater 540 are formed. Typically, such holes are 200-500 μm in diameter, but it should be understood that the size of or method of constructing the hole may vary. Preferred means for drilling the holes are related to the desired diameter. For holes 300 μm and greater, mechanical drilling or ultrasonic drilling is preferred, although laser drilling also works. Laser drilling presently works for holes as small as 200 μm in diameter; recent research indicates that laser drilling may also work for holes as small as 50 μm in diameter, or smaller.

Leads 565 may be run through the holes either by electroplating or by squeezing conductive materials (e.g., pastes) through the holes using screen-printing techniques. Materials for electroplating include aluminum, gold, and nickel, as known in the art. Materials for conductive paste include silver-filled epoxy, although other pastes are known to those skilled in the art to be appropriate.

Figure 17:
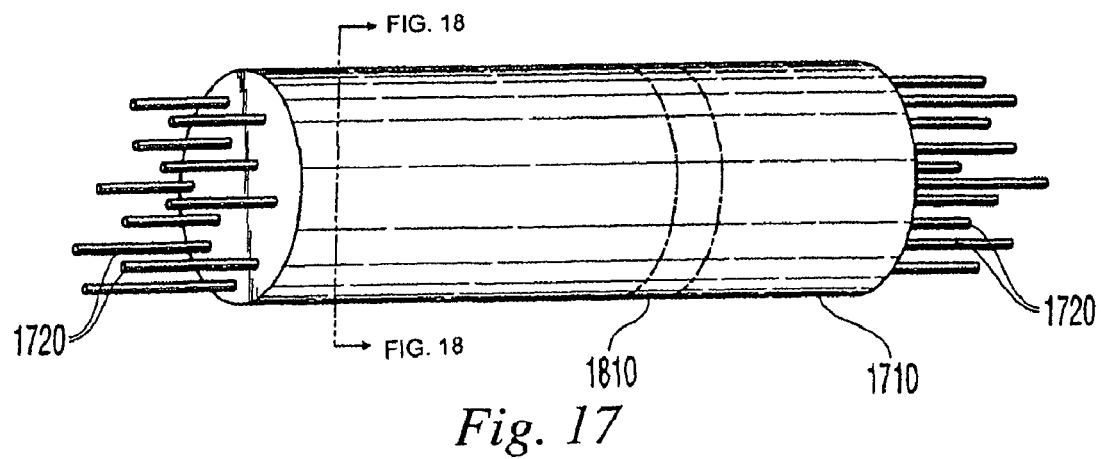
FIG. 17 depicts a cylinder of substrate material comprising wires that run parallel to the axis of the cylinder and that are spaced cross-sectionally as the vertical leads are desired to be spaced in the substrate.
Figure 18:
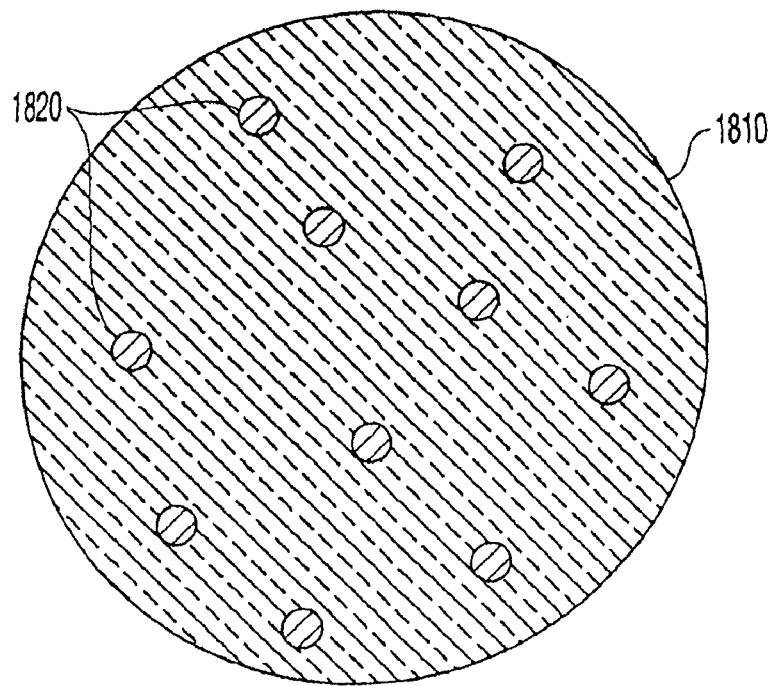
FIG. 18 depicts a lead-gridded substrate formed by slicing the cylinder depicted in FIG. 17 into a cross-section of the desired thickness.

An alternative method of creating the vertical leads 565 is to form a substrate that comprises a "grid" of vertical leads, such as shown in FIG. 18. Referring to FIG. 17, such a "lead-gridded" substrate 1810 is preferably fabricated by stretching a plurality of wires through a tabular shaped mold 1710, with the wires spaced in the same spacing desired for the intended leads. (Alternatively, the leads can be laid out in a rectangular matrix, for example, and the heater leads run to the nearest pair of vertical leads). Then, a substrate material (such as plastic) is injected into the tube 1710 (or an elongated quadrilateral or another shape appropriate to the method described herein) and surrounds the wires 1720. The result is a cylinder of substrate material comprising wires 1720 that run parallel to the axis of the tube and that are spaced cross-sectionally as the vertical leads are desired to be spaced in the substrate. See FIG. 17. Then, to obtain a lead-gridded substrate, the remaining steps are to slice the cylinder into a cross-section 1810 of the desired thickness and polish as necessary. See FIG. 18. Those skilled in the art will recognize the cost efficiency of this method, in that multiple lead-gridded substrates (of uniform or varying thicknesses) can be obtained from a single wired cylinder of the type shown in FIG. 17.

Referring to FIGS. 13-15, unwanted heat transfer from the leads to a microfluidic complex 110 may also be reduced by substantially decreasing the current density in the leads relative to the current density in the heating elements. In the structure shown in FIGS. 13-15, this is accomplished by providing the leads with a greater thickness than the conductors of the heater element 540. For example, as shown in FIGS. 14,15, the leads 1360 are substantially thicker than the conductor which forms the heating element 540. Increasing the vertical thickness of the lead wires increases the cross-sectional area of the lead wires, thus decreasing the electrical resistance of the wires. This also decreases the current density within the leads and thereby decreases the amount of heat radiated by the leads when a given current is applied.

Figure 16:
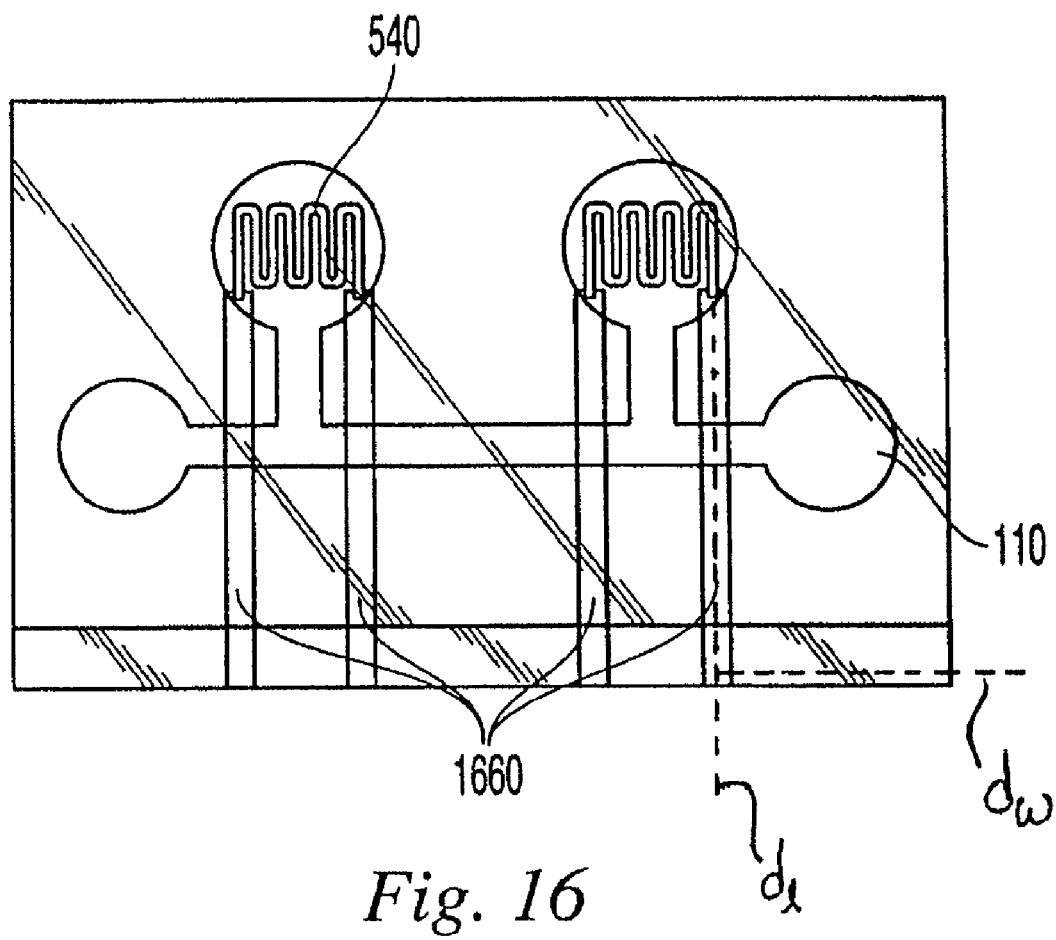
FIG. 16 depicts a top-down view of a device comprising a further preferred embodiment of the present invention.

Referring to FIG. 16, heat transfer from the leads to a microfluidic complex 110 may also be reduced by increasing the horizontal thickness of the electric leads 1660 that connect heater elements 540 to a power source. Here, "horizontal" means in a direction parallel to the plane in which oxide layer 150 lies (refer to FIG. 15, for example). The leads 1660 have a length taken along a dimension $d_l$, which is parallel to the plane in which oxide layer 150 lies. Leads 1660 are thicker than heater element 540 along a dimension $d_w$, which is parallel to the plane in which oxide layer 150 lies and orthogonal to dimension $d_l$, of the leads. The preferred configuration is similar to that shown in FIGS. 2-4. However, the improvement comprised in the embodiment shown in FIGS. 16 lies in the increased horizontal thickness of leads 1660. Increasing the horizontal thickness of the leads increases the cross-sectional area of the lead wires, thus decreasing the electrical resistance of the wires. This in turn decreases the amount of heat radiated by the wires when a given current is applied, thus decreasing the amount of heat transferred from the wires to microfluidic complex 110.

An advantage of increasing the horizontal thickness instead of the vertical thickness is that there is less likely to be a need to increase the thickness of the oxide layer 150. On the other hand, an advantage of increasing the vertical thickness instead of the horizontal thickness is that a greater number of leads can be used on the substrate without interfering with each other.

In a still further embodiment, the thickness of the leads is increased in both the horizontal and vertical directions. Those skilled in the art will recognize that the leads can be modified in a variety of ways without departing from the scope of the invention, as long as it results in a substantial decrease in the current density within the leads (relative to the current density in the heating elements) to thereby reduce the amount of heat transferred from the leads to the microfluidic complex to an acceptable level (i.e., a level that does not significantly interfere with the operation of the microfluidic complex).

Other embodiments comprise combinations of the elements above that will be clear to those skilled in the art. For example, the vertical feed through, shown in FIGS. 5-7, can be combined with the thickened leads, (FIGS. 13-16), so that the leads 565 (see, e.g., FIG. 7) that are run "vertically" through the substrate 130 are increased in thickness, to further reduce heat emitted by the leads 565 and potentially transferred to the microfluidic complex 110. Similarly, the leads 560 (again, see FIG. 7) that run along the lower side of substrate 130 can also be increased in thickness to reduce heat emitted by the leads 560 that could be transmitted to the microfluidic complex 110, although preferably the substrate 130 is comprised of material with a thermal conductivity low enough to make such a modification unnecessary.

The amount of heat in a microfluidic complex may also be controlled using one or more Peltier devices. See FIGS. 8-12.

Such devices can be made to act as heat pumps, removing unwanted heat from a microfluidic complex or component thereof. Peltier devices are well-known (see U.S. Pat. No. 5,714,701, to Chi et al., for example). Peltier discovered the effect that bears his name in 1834. Modem Peltier devices (also known as thermoelectric cooling devices) are typically composed of segments of heavily-doped semiconductors (often bismuth telluride) that are connected electrically in series and thermally in parallel between the heated and cooled surfaces of the device. Such devices are available commercially, for example, from MELCOR, 1040 Spruce Street, Trenton, N.J. 08648; see also http://www.melcor.com.

In this second preferred embodiment, at least one Peltier device 810 is attached to the substrate 130, although in an alternate embodiment at least one Peltier device 910 (see FIG. 9) is attached to the upper substrate 120 of a preferred microfluidic device. This "upper" Peltier device 910 can be in addition or an alternative to any "lower" Peltier devices 810 attached to the substrate 130. Preferred Peltier devices are battery-operated, and are attached to substrate 130 or substrate 120 using a heat-transfer paste, to improve heat conduction. In this embodiment, a Peltier device is used to cool an entire microfluidic chip. As discussed below, Peltier devices are used in other embodiments to cool selected areas of a chip, sometimes cooling different areas at different times, depending on the preferred operation of a microfluidic complex in the chip.

Figure 10:
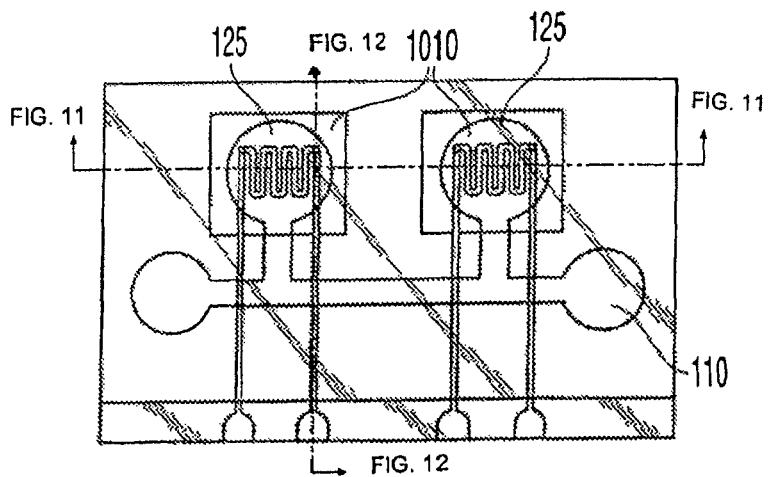
FIG. 10 depicts the device in FIG. 5, with multiple Peltier devices attached to the lower substrate.

Peltier devices are preferably used to remove heat primarily from selected areas of a microfluidic complex. For example, unnecessary power consumption would result if a Peltier device was cooling the entire substrate at the same time that a heater element was attempting to heat a selected chamber in the substrate. By using a plurality of Peltier devices, controlled electronically, heat can be removed from selected areas of a microfluidic complex while allowing other areas to be heated with a minimum of consumed power. FIG. 10 shows two Peltier devices 1010 attached to the bottom of substrate 130 so as to be capable of cooling selected areas (microchambers 125) of a microfluidic complex in substrate 120. The depicted configuration is, of course, merely exemplary—any operable configuration of multiple Peltier devices, where the Peltier devices are of any compatible collection of shapes, would also work in this embodiment. Further, although the depicted configuration is for a chip with heater leads as in FIGS. 5-7, a multiple-Peltier-device configuration can also be used on a microfluidic device such as that depicted in FIGS. 2-4. Multiple Peltier devices 910 can be similarly configured on the top substrate 120 of a microfluidic device. Peltier devices can be used to cool an entire microfluidic chip, an entire microfluidic complex, or selected portions (channels, chambers, etc.) thereof, and different Peltier devices can be used at different times, depending on desired functionality of the microfluidic complex.

Figure 11:
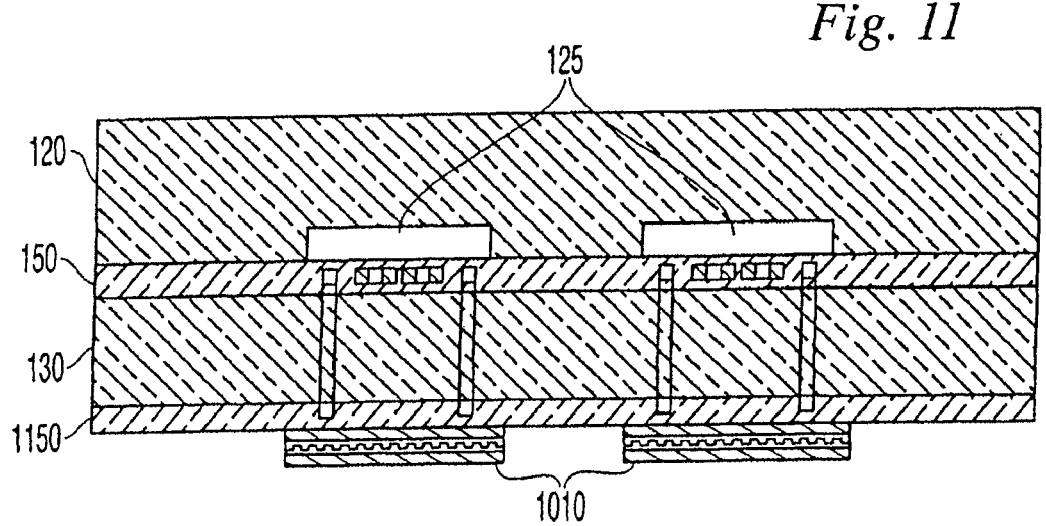
FIG. 11 depicts a cross-sectional end view of the device in FIG. 10.
Figure 12:
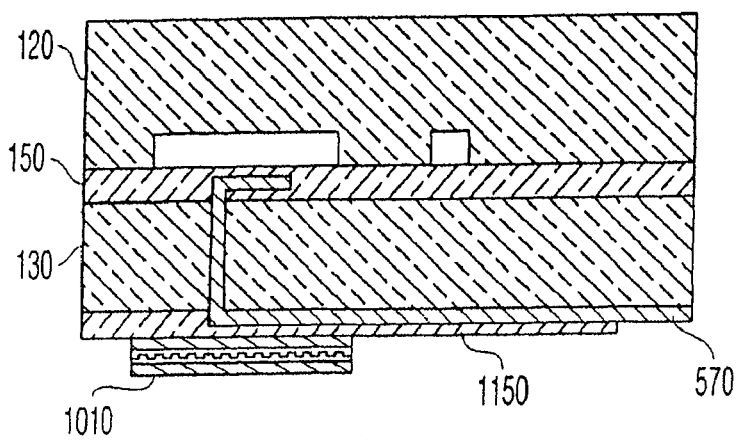
FIG. 12 depicts a cross-sectional side view of the device in FIG. 10.

FIGS. 11 and 12 depict cross-sectional views of the device in FIG. 10. A silicon oxide layer 1150 covers heater leads 560. A heat-transfer paste lies between silicon oxide layer 1150 and Peltier devices 1010.

While the operations described above have been for simple designs, the present invention contemplates more complicated devices involving the introduction of multiple samples and the movement of multiple microdroplets (including simultaneous movement of separate and discrete droplets), as well as multiple microchannels and microchambers, and potentially including meltable materials. Furthermore, as discussed above, those skilled in the art will recognize that the subject invention is not limited to microfluidic devices comprised of one glass substrate bound to another, or to microfluidic complexes formed by etching or otherwise forming chambers and channels into the bottom surface of an upper substrate that is then bonded to a lower substrate, or even to microfluidic devices formed by bonding one substrate to another. The present invention will be recognized by those skilled in the art as applying to any microfluidic device that comprises a microfluidic complex having a heating region.

Moreover, although much of the above description depicts, for simplicity of explanation, two leads running from each heater element, it is possible to share leads among heater elements so that, for example, two heater elements can be served by three leads (e.g., with the shared lead serving as a common ground).

What is claimed is:

1. An integrated microfluidic processing system comprising a microfluidic device, the device comprising:
   a microfluidic complex comprising at least one thermally actuated component, wherein at least one thermally actuated component is configured for moving fluid in the microfluidic device;
   a thermally insulating substrate comprising a heating element configured to actuate the thermally actuated component;
   at least one conductive lead for supplying electrical current from a current source to the heating element, wherein the lead has a lower current density that the heating element; and
   a Peltier cooler configured to remove heat from specific regions of the microfluidic complex.

2. An integrated microfluidic system comprising a microfluidic device, the device comprising:
   first and second substrates defining, therebetween, a microfluidic complex;
   at least one heating element configured to heat a portion of the microfluidic complex, at least one heating element further configured for moving fluid in the microfluidic device;
   at least one conductive lead for supplying electrical current from a current source to the heating element, wherein the lead has a lower current density that the heating element; and
   one or more Peltier devices abutting one or both of the first and second substrates.

3. The system of claim 2, wherein the one or more Peltier devices are attached to the substrates with a heat-transfer paste.

4. The system of claim 2, wherein at least one of the Peltier devices is configured to cool the entire microfluidic complex.

5. The system of claim 2, wherein at least one of the Peltier devices is configured to cool a specific region of the microfluidic complex.

6. The system of claim 5, wherein the specific region includes a microchamber in the microfluidic complex.

7. The system of claim 2, comprising multiple Peltier devices abutting one of the first and second substrates.

8. The system of claim 2, comprising two or more Peltier devices, wherein the two or more Peltier devices are independently controllable.

9. The system of claim 2, wherein the heating element is contained within an insulating layer disposed between the first and second substrates.

10. The system of claim 2, further comprising an insulating layer adjacent one of the first and second substrates, wherein at least one of the one or more Peltier devices is attached to the insulating layer.

11. The system of claim 2, wherein the one or more Peltier devices are controlled electronically, or are battery operated.

12. The system of claim 2, further comprising a conductor in electrical communication with the heating element wherein at least a portion of the conductor is separated from the microfluidic complex by one of the first or second substrates.

* * * * *